US012655321B2

(12) United States Patent
Choi et al.

(10) Patent No.: US 12,655,321 B2
(45) Date of Patent: Jun. 16, 2026

(54) COMPOUND, CMP SLURRY COMPOSITION INCLUDING THE SAME AND POLISHING METHOD USING THE SAME

(71) Applicant: SAMSUNG SDI CO., LTD., Yongin-si (KR)

(72) Inventors: Se Young Choi, Suwon-si (KR); Yong Goog Kim, Suwon-si (KR); Soo Yeon Sim, Suwon-si (KR); Ja Young Hwang, Suwon-si (KR); Jeong Hee Kim, Suwon-si (KR); Youn Jin Cho, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 667 days.

(21) Appl. No.: 18/074,856

(22) Filed: Dec. 5, 2022

(65) Prior Publication Data

US 2023/0227695 A1 Jul. 20, 2023

(30) Foreign Application Priority Data

Jan. 19, 2022 (KR) ........................ 10-2022-0007624

(51) Int. Cl.

*C09G 1/02* (2006.01)
*C07D 249/08* (2006.01)
*C07D 403/12* (2006.01)
*C09K 15/30* (2006.01)

(52) U.S. Cl.

CPC ............. *C09G 1/02* (2013.01); *C07D 249/08* (2013.01); *C07D 403/12* (2013.01); *C09K 15/30* (2013.01)

(58) Field of Classification Search

CPC ...... C09G 1/02; C07D 249/08; C07D 403/12; C07D 249/18; C07D 249/14; C09K 15/30; C09K 3/1463; C09K 3/1481; C23F 3/04; H01L 21/4821; H01L 21/4846; H01L 21/76838

See application file for complete search history.

(56) References Cited

U.S. PATENT DOCUMENTS

| | | | |
|---|---|---|---|
| 3,431,251 A | 3/1969 | Hauser | |
| 5,889,161 A | 3/1999 | Bottaro et al. | |
| 2007/0293048 A1 | 12/2007 | Lee et al. | |
| 2010/0115710 A1* | 5/2010 | Hayama ................. | A61K 8/496 8/405 |
| 2015/0118845 A1 | 4/2015 | Noller et al. | |
| 2019/0085208 A1 | 3/2019 | Shinoda et al. | |

FOREIGN PATENT DOCUMENTS

| | | |
|---|---|---|
| CN | 102477262 A | 5/2012 |
| CN | 107674099 A | 2/2018 |
| CN | 110819237 A | 2/2020 |
| CN | 113549399 A | 10/2021 |
| JP | S 55-047374 A | 4/1980 |
| JP | 05001250 A | 1/1993 |
| JP | H 05-125060 A | 5/1993 |
| JP | 2008-291019 A | 12/2008 |
| JP | 2011-080070 A | 4/2011 |
| JP | 2013-185166 A | 9/2013 |
| KR | 10-2019-0081988 A | 7/2019 |
| TW | 202003783 A | 1/2020 |

OTHER PUBLICATIONS

Taiwanese Office Action issued on Aug. 28, 2023, in the corresponding Taiwanese Patent Application No. 111148223.

4.Yanxuan Qiu et al., ‘Syntheses, structures, electrochemical and optical properties of four transition metal complexes based on the 1-triazolyl-3-benzimidazolyltriazene ligand’, This journal is © The Royal Society of Chemistry 2016, vol. 9, pp. 4969-4978 (Jan. 5, 2016).

5.Yixin He et al., ‘Azobispyrazole family as photoswitches combining (near-)quantitative bidirectional isomerization and widely tunable thermal half-lives from hours to years’, pp. 1-15 (Mar. 3, 2021).

6.Sanjib Panda et al., ‘Inner-sphere electron transfer at the ruthenium-azo interface’, This journal is © The Royal Society of Chemistry 2022, vol. 51, pp. 2547-2559, (Jan. 11, 2022).

Chinese Office action dated Mar. 8, 2025.

Gehlen, Heinz; et al., Nitrosamines of 3-amino-1,2,4-triazoles, Justus Liebigs Annalen der Chemie, 1963, 665, 144-9.

Heitke, Bruce T.; McCarty, C. Gordon, Syntheses of C-amino- and C-azido-1,2,4-triazoles, Journal of Organic Chemistry, 1974, 39(11), 1522-6.

Hanot, Vincent P., et al., Crystal structure, magnetic properties and spectroscopic studies of bis[1,3-bis(pyrazol-3-yl)triazenido]dicopper(II) trihydrate: a dinuclear complex with an asymmetric double pyrazolate bridge, Journal of the Chemical Society, Dalton Transactions: Inorganic Chemistry, 1996,(22), 4275-4281.

Zhao, Xiuxiu, et al., The stability and decomposition mechanism of the catenated nitrogen compounds, Journal of Molecular Modeling, 2015, 21(9), 1-6.

Lai, Wei-Peng, et al., A density functional theory study on the structures and thermochemical properties of azo-bridged azoles, Hanneng Cailiao, 2016, 24(9), 842-847.

Wu, Xiaowei, et al., Cis-Trans Isomerization and Thermal Decomposition Mechanisms of a Series of Nx (x=4, 8, 10, 11) Chain-Catenated Energetic Crystals, Journal of Physical Chemistry A, 2021, 125(14), 2826-2835.

(Continued)

*Primary Examiner* — Andrew J. Oyer
(74) *Attorney, Agent, or Firm* — Lee IP Law, P.C.

(57) ABSTRACT

A compound or a salt thereof, a CMP slurry composition including the same, and a polishing method using the same, the compound being represented by Formula 1,

[Formula 1]

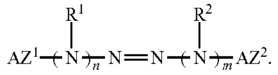

11 Claims, No Drawings

(56) References Cited

OTHER PUBLICATIONS

Japanese Office Action issued on Dec. 4, 2023, in the corresponding Japanese Patent Application No. 2022-194885.
Korean Notice of Allowance dated Aug. 21, 2025.
Chinese Office action dated Nov. 27, 2025.

* cited by examiner

COMPOUND, CMP SLURRY COMPOSITION INCLUDING THE SAME AND POLISHING METHOD USING THE SAME

CROSS-REFERENCE TO RELATED APPLICATION

This application claims the benefit of Korean Patent Application No. 10-2022-0007624, filed on Jan. 19, 2022, in the Korean Intellectual Property Office, the entire disclosure of which is incorporated herein by reference.

BACKGROUND

1. Field

Embodiments relate to a compound, a CMP slurry composition including the same, and a polishing method using the same.

2. Description of the Related Art

For a process of polishing a copper layer acting as metal interconnects of a semiconductor device, it may be desirable to achieve a sufficient polishing rate, better polishing selectivity than a barrier metal or dielectrics, suitable polishing flatness, and low defect rate.

By way of summation and review, a CMP slurry composition may be capable of realizing high flatness with reduction in interconnects and layer thickness for formation of fine patterns.

Improvement in polishing flatness may be achieved by various methods, such as increase in amount of a corrosion inhibitor, use of a polymer film-forming agent, or a reduction in size or amount of abrasive particles. However, these methods may have a trade-off between the polishing rate and dishing through decrease in copper polishing rate. Triazole or tetrazole compounds may be used as a corrosion inhibitor. The triazole compound or the tetrazole compound may provide a certain degree of anticorrosion performance when used in large amounts, and these compounds may have a relatively low polishing rate.

SUMMARY

The embodiments may be realized by providing a compound represented by Formula 1, or a salt thereof,

[Formula 1]

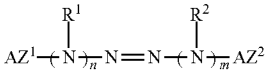

wherein, in Formula 1, $AZ^1$ and $AZ^2$ are each independently a substituted or unsubstituted azole-containing heterocyclic group; $R^1$ and $R^2$ are each independently hydrogen, a substituted or unsubstituted $C_1$ to $C_{10}$ alkyl group, a substituted or unsubstituted $C_6$ to $C_{20}$ aryl group, a substituted or unsubstituted $C_7$ to $C_{20}$ arylalkyl group, or a substituted or unsubstituted $C_3$ to $C_{20}$ heteroaryl group; and n and m are each independently an integer of 0 to 2.

The azole-containing heterocyclic group may be a monocyclic azole-containing heterocyclic group having 1 to 6 nitrogen atoms or a polycyclic azole-containing heterocyclic group having 1 to 6 nitrogen atoms.

The azole-containing heterocyclic group may be a diazole group, a triazole group, a tetrazole group, a pentazole group, a benzodiazole group, a benzotriazole group, or a naphthotriazole group.

The compound represented by Formula 1 may be represented by one of Formulae 1-1 to 1-4:

[Formula 1-1]

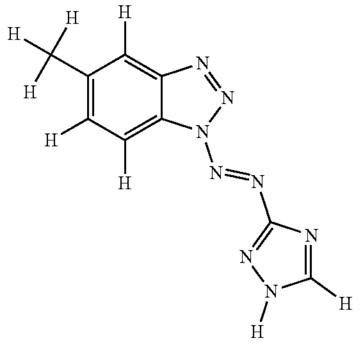

[Formula 1-2]

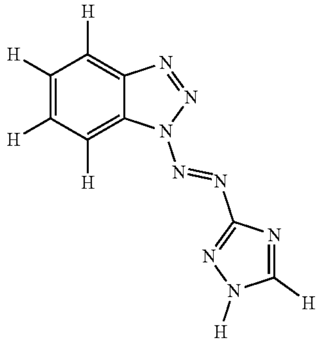

[Formula 1-3]

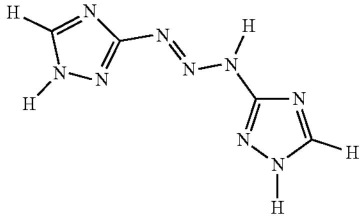

[Formula 1-4]

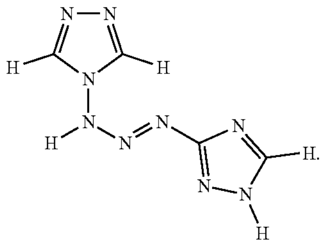

The compound or the salt thereof may be used as a corrosion inhibitor in a CMP composition.

The embodiments may be realized by providing a CMP slurry composition including a polar solvent or a non-polar solvent; an abrasive agent; and a corrosion inhibitor, wherein the corrosion inhibitor includes the compound or salt thereof according to an embodiment.

The CMP slurry composition may include 0.001 wt % to 5 wt % of the corrosion inhibitor.

The corrosion inhibitor may further include a diazo group-free corrosion inhibitor.

The diazo group-free corrosion inhibitor may include a triazole corrosion inhibitor or a tetrazole corrosion inhibitor.

The CMP slurry composition may further include a complexing agent or an oxidizing agent.

The CMP slurry composition may include 0.001 wt % to 20 wt % of the abrasive agent; 0.001 wt % to 5 wt % of the corrosion inhibitor; 0.01 wt % to 20 wt % of the complexing agent; and 0.1 wt % to 5 wt % of the oxidizing agent.

The embodiments may be realized by providing a polishing method including polishing a polishing target using the CMP slurry composition according to an embodiment.

The polishing target may be a copper layer.

DETAILED DESCRIPTION

The embodiments may provide a compound represented by Formula 1, or a salt thereof. In an implementation, the compound may be an azo compound, a diazo compound, a diazene compound, or the like.

[Formula 1]

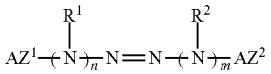

In Formula 1, $AZ^1$ and $AZ^2$ may each independently be or include, e.g., a substituted or unsubstituted azole-containing heterocyclic (e.g., heteroaryl) group.

$R^1$ and $R^2$ may each independently be or include, e.g., hydrogen, a substituted or unsubstituted $C_1$ to $C_{20}$ alkyl group, a substituted or unsubstituted $C_6$ to $C_{20}$ aryl group, a substituted or unsubstituted $C_7$ to $C_{20}$ arylalkyl group, or a substituted or unsubstituted $C_3$ to $C_{20}$ heteroaryl group.

n and m may each independently be, e.g., an integer of 0 to 2.

As used herein, "substituted" in "substituted or unsubstituted" means that at least one hydrogen atom in a corresponding functional group is substituted with a $C_1$ to $C_{10}$ alkyl group, a $C_6$ to $C_{20}$ aryl group, a $C_7$ to $C_{20}$ arylalkyl group, a $C_3$ to $C_{20}$ heteroaryl group, a $C_3$ to $C_{10}$ alicyclic group, a hydroxyl group, an amino group, or the like. As used herein, the term "or" is not an exclusive term, e.g., "A or B" would include A, B, or A and B.

The compound of Formula 1 may be used as, e.g., a corrosion inhibitor. In the CMP slurry composition, the corrosion inhibitor may help reduce a corrosion rate of a polishing target. In an implementation, the compound of Formula 1 may include, e.g., two azole-containing heterocyclic groups, in which the azole-containing heterocyclic groups are connected to an azo, diazene, diazo, or the like, group, to help minimize reduction in polishing rate while improving polishing flatness through reduction in erosion upon polishing.

In an implementation, the compound of Formula 1 may be included as the corrosion inhibitor in the CMP slurry composition to help minimize reduction in polishing rate while improving polishing flatness through reduction in erosion and the like. In an implementation, the compound of Formula 1 may be the corrosion inhibitor upon polishing a metal layer, e.g., a copper layer.

In an implementation, in Formula 1, the azole-containing heterocyclic group may be a monocyclic or polycyclic azole-containing heterocyclic group having 1 to 6 nitrogen atoms. Here, "polycyclic" means an azole-containing heterocyclic group containing at least two aryl groups, in which at least one of the aryl groups is a heteroaryl group having a nitrogen atom as an element constituting a ring and the at least two aryl groups are fused to each other or connected to each other through a single bond or a $C_1$ to $C_{10}$ alkylene group. The azole-containing heterocyclic group may have 10 or fewer ring carbon atoms.

In an implementation, the azole-containing heterocyclic group may be, e.g., a heteroaryl group having one ring nitrogen atom, a heteroaryl group having two ring nitrogen atoms, a heteroaryl group having three ring nitrogen atoms, a heteroaryl group having four ring nitrogen atoms, or a heteroaryl group having five ring nitrogen atoms. The heteroaryl group may have 6 or fewer ring carbon atoms.

In an implementation, the azole-containing heterocyclic group may be, e.g., a diazole group such as imidazole group, pyrazole group, or the like; a triazole group such as 1,2,3-triazole group, 1,2,4-triazole group, or the like, a tetrazole group, a pentazole group, a benzodiazole group, a benzotriazole group, or a naphthotriazole group. In an implementation, the azole-containing heterocyclic group may be, e.g., a benzotriazole group, 1,2,3-triazole group, 1,2,4-triazole group, or the like.

At least part of the azole-containing heterocyclic group may be hydrogenated.

In an implementation, in Formula 1, n and m may each independently be, e.g., 0, 1, or 2.

In an implementation, in Formula 1, $R^1$ and $R^2$ may each independently be, e.g., hydrogen, a substituted or unsubstituted $C_1$ to $C_5$ alkyl group, a substituted or unsubstituted $C_6$ to $C_{10}$ aryl group, a substituted or unsubstituted $C_7$ to $C_{10}$ arylalkyl group, or a substituted or unsubstituted $C_3$ to $C_{10}$ heteroaryl group. In an implementation, in Formula 1, $R^1$ and $R^2$ may each be, e.g., hydrogen.

In an implementation, the compound of Formula 1 may consist of carbon, nitrogen, and hydrogen.

In an implementation, the compound of Formula 1 may be represented by, e.g., one of the following Formulae 1-1 to 1-4:

[Formula 1-1]

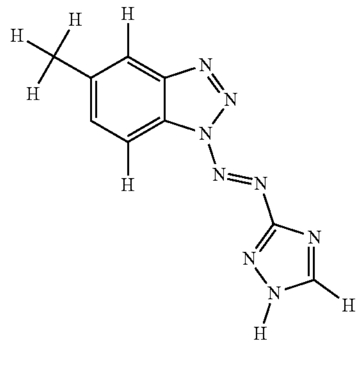

-continued

[Formula 1-2]

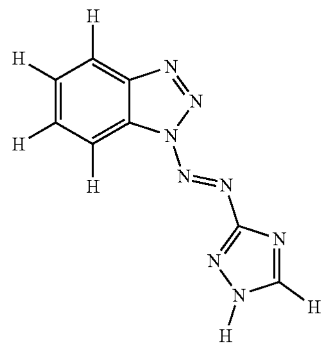

[Formula 1-3]

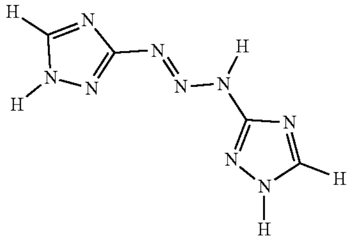

[Formula 1-4]

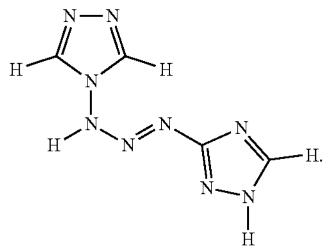

The salt of the compound of Formula 1 may be prepared through reaction of an acid or a base with the compound of Formula 1.

The compound of Formula 1 may be prepared by a suitable method. In an implementation, the compound of Formula 1 may be prepared by producing an azo group, a diazene group, a diazo group, or a diazonium group in an azole compound having an amino group through diazotization of the azole compound, followed by, e.g., diazo coupling or diazonium coupling with another azole compound.

A CMP slurry composition according to an embodiment may include, e.g., a solvent (e.g., a polar solvent or a non-polar solvent); an abrasive agent; and a corrosion inhibitor. The corrosion inhibitor may include the compound of Formula 1 or the salt thereof described above. In an implementation, the CMP slurry composition may help improve flatness of a polishing target through reduction in erosion and the like, while improving polishing rate with respect to the polishing target. The CMP slurry composition according to an embodiment may help maintain a high polishing rate with respect to the polishing target while improving polishing flatness thereof, as compared with a composition not containing the corrosion inhibitor described above. The CMP slurry composition may be applied to a process of polishing a metal layer, e.g., a copper layer.

Next, the components of the CMP slurry composition according to an embodiment (hereinafter referred to as "CMP slurry composition") will be described in detail.

The corrosion inhibitor may include, e.g., a compound of Formula 1 or a salt thereof. The compound of Formula 1 or the salt thereof is described above. Even with a smaller amount of the compound of Formula 1 or the salt thereof than other triazole or tetrazole corrosion inhibitors, the compound of Formula 1 or the salt thereof may achieve significant improvement in polishing flatness.

In an implementation, the compound of Formula 1 or the salt thereof may be present in an amount of 1 wt % to 100 wt %, e.g., 5 wt %, 6 wt %, 7 wt %, 8 wt %, 9 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 100 wt %, or 5 wt % to 100 wt %, based on the total weight of all corrosion inhibitors in the CMP slurry composition. Within these ranges, the compound of Formula 1 or the salt thereof may help secure inherent effects thereof in the CMP slurry composition.

In an implementation, the corrosion inhibitor may further include another corrosion inhibitor (e.g., different from the compound represented by Formula 1), e.g., a diazo or diazene group-free corrosion inhibitor. The other corrosion inhibitor may include, e.g., a triazole corrosion inhibitor or a tetrazole corrosion inhibitor.

The triazole corrosion inhibitor may include, e.g., a triazole, such as 1,2,4-triazole, 1,2,3-triazole, or the like; a diaminotriazole, such as 3,5-diamino-1,2,4-triazole, or the like, a methyl benzotriazole, such as 5-methylbenzotriazole, 4-methylbenzotriazole, or the like, or a benzotriazole based compound, such as ethyl benzotriazole, propyl benzotriazole, butyl benzotriazole, pentyl benzotriazole, hexyl benzotriazole, or the like. The triazole corrosion inhibitor may be present in the form of the triazole corrosion inhibitor per se or in the form of a salt of the triazole corrosion inhibitor in the CMP slurry composition.

The tetrazole corrosion inhibitor may include, e.g., tetrazole, 5-aminotetrazole, 5-methyltetrazole, or 5-phenyltetrazole. The tetrazole corrosion inhibitor may be present in the form of the tetrazole corrosion inhibitor per se or in the form of a salt of the tetrazole corrosion inhibitor.

In an implementation, in the CMP slurry composition, the corrosion inhibitor may be present in an amount of, e.g., 0.001 wt % to 5 wt %, for 0.001 wt %, 0.01 wt %, 0.05 wt %, 0.1 wt %, 0.15 wt %, 0.2 wt %, 0.25 wt %, 0.3 wt %, 0.35 wt %, 0.4 wt %, 0.45 wt %, 0.5 wt %, 0.55 wt %, 0.6 wt %, 0.65 wt %, 0.7 wt %, 0.75 wt %, 0.8 wt %, 0.85 wt %, 0.9 wt %, 0.95 wt %, 1 wt %, 1.5 wt %, 2 wt %, 2.5 wt %, 3 wt %, 3.5 wt %, 4 wt %, 4.5 wt %, 5 wt %, or 0.005 wt % to 0.5 wt %. Within these ranges, the corrosion inhibitor may help increase the polishing rate while improving polishing flatness through reduction in erosion and the like upon polishing.

The solvent (e.g., the polar solvent or the non-polar solvent) may help reduce friction on the polishing target upon polishing the polishing target with an abrasive agent. In an implementation, the solvent may include, e.g., water (e.g., ultrapure water), an organic amine, an organic alcohol, an organic alcohol amine, an organic ether, an organic ketone, or the like. In an implementation, the solvent may include, e.g., ultrapure water or deionized water. In an implementation, the solvent may be present in a balance amount of the CMP slurry composition. In an implementation, the solvent may be present in an amount of, e.g., 30 wt % to 98 wt %, based on a total weight of the CMP slurry composition.

The abrasive agent may include a suitable abrasive agent for polishing. In an implementation, the abrasive agent may include oxide abrasive particles of metals or non-metals. In an implementation, the abrasive agent may include, e.g., silica including colloidal silica or fumed silica, alumina, ceria, titania, or zirconia. In an implementation, the abrasive agent may include silica (e.g., colloidal silica).

In an implementation, the abrasive agent may include, e.g., spherical or non-spherical particles, in which primary particles have an average particle diameter (D50) of 10 nm to 150 nm, e.g., 20 nm to 70 nm. Within this range, the CMP slurry composition may help secure a sufficient polishing rate with respect to a polishing target without generation of scratches while improving flatness after polishing. Here, "average particle diameter (D50)" means the diameter of particles corresponding to 50% by volume in a volume distribution of the abrasive agent.

The abrasive agent may be subjected to surface modification or not be subjected to surface modification. The surface-modified abrasive agent may help further improve dispersion stability or polishing rate of the abrasive agent in the CMP slurry composition. Surface modification of the abrasive agent may be performed by treating the abrasive agent with a compound for surface modification. The compound for surface modification may include a silane compound. The silane compound may facilitate surface modification when the abrasive agent is silica. In an implementation, the silane compound may include, e.g., a mercapto group-containing alkoxysilane, an amino group-containing alkoxysilane, a tetraalkoxysilane, or an alkoxysilane containing an alkyl group having a $C_1$ to $C_{10}$ alkyl group.

In the CMP slurry composition, the abrasive agent may be present in an amount of, e.g., 0.001 wt % to 20 wt %, 0.005 wt % to 10 wt %, 0.01 wt % to 5 wt %, or 0.05 wt % to 3 wt %. Within these ranges, the CMP slurry composition may help secure a sufficient polishing rate with respect to a polishing target without generation of scratches while securing dispersion stability thereof.

In an implementation, the CMP slurry composition may further include, e.g., a complexing agent or an oxidizing agent.

The complexing agent promotes chelation of metal cations and metal oxides generated upon polishing. As a result, the complexing agent may help suppress adsorption of the metal oxide to a polishing target and generation of surface defects while improving the polishing rate with respect to the polishing target.

The complexing agent may include, e.g., an organic acid or salts thereof, an amino acid or salts thereof, alcohols, such as a dialcohol, a trialcohol or a polyalcohol, an amine-containing compound, phosphate, or a phosphate salt. In an implementation, an amino acid may be used as the complexing agent. Here, "organic acid" means an acid free from an amino group ($-NH_2$), compared with the amino acid. As the complexing agent, the amino acid may help secure a higher polishing rate with respect to a polishing target than the organic acids or salts thereof, and the phosphate salts.

The organic acid may include an organic carboxylic acid containing at least one (e.g., one or two) carboxylic acid groups. In an implementation, the organic acid may include a saturated acid, such as glycolic acid, lactic acid, acetic acid, propionic acid, butyric acid, pentanoic acid, hexanoic acid, formic acid, salicylic acid, dimethyl butyric acid, octanoic acid, benzoic acid, oxalic acid, malonic acid, succinic acid, glutaric acid, adipic acid, pimelic acid, or the like, maleic acid, fumaric acid, itaconic acid, phthalic acid, citric acid, or the like. In an implementation, the salts of the organic acid may include ammonium citrate, ammonium acetate, or the like.

The amino acid may include, e.g., glycine, alanine, serine, asparagine, glutamic acid, proline, oxyproline, arginine, cysteine, histidine, tyrosine, leucine, lysine, methionine, valine, isoleucine, threonine, tryptophan, or phenylalanine. In an implementation, the amino acid may be, e.g., glycine, to further improve the polishing rate with respect to a copper layer.

The phosphate salt may include, e.g., triammonium phosphate, triammonium phosphate trihydrate, or the like.

In the CMP slurry composition, the complexing agent may be present in an amount of, e.g., 0.01 wt % to 20 wt %, or 0.1 wt % to 10 wt %. Within these ranges, the complexing agent may help improve the polishing rate with respect to the polishing target, dispersion stability of the slurry composition, and surface characteristics of the polishing target.

The oxidizing agent serves to oxidize the polishing target to facilitate polishing of the polishing target and forms a uniform surface of the polishing target such that the polishing target can have good surface roughness even after polishing.

The oxidizing agent may include, e.g., an inorganic percompound, an organic percompound, bromic acid or salts thereof, nitric acid or salts thereof, chloric acid or salts thereof, chromic acid or salts thereof, iodic acid or salts thereof, iron or salts thereof, copper or salts thereof, rare-earth metal oxides, transition metal oxides, or potassium dichromate. Here, the "percompound" refers to a compound that contains at least one peroxide group ($-O-O-$) or an element in the highest oxidation state. In an implementation, the oxidizing agent may be a percompound. In an implementation, the percompund may include, e.g., hydrogen peroxide, potassium periodide, calcium persulfate, or potassium ferricyanide. In an implementation, the percompund may include, e.g., hydrogen peroxide.

In the CMP slurry composition, the oxidizing agent may be present in an amount of, e.g., 0.1 wt % to 5 wt %, or 0.5 wt % to 3 wt %. Within these ranges, the CMP slurry composition may help secure polishing effects.

In an implementation, the CMP slurry composition may further include a pH regulator. The pH regulator may include an organic base, e.g., sodium hydroxide, potassium hydroxide, ammonium hydroxide, sodium carbonate, or potassium carbonate. The pH regulator may include an inorganic acid, e.g., nitric acid, phosphoric acid, hydrochloric acid, or sulfuric acid. In the CMP slurry composition, the pH regulator may be optionally present, e.g., in an amount of 1 wt % or less.

The CMP slurry composition may further include suitable additives, e.g., surfactants, dispersants, modifiers, surface active agents, or the like.

In an implementation, the CMP slurry composition may have a pH of, e.g., 5 to 9, or 6 to 8.

Another embodiment provides a polishing method that includes polishing a polishing target (e.g., a copper layer) using the CMP slurry composition.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE 1

0.084 g (0.001 mol) of 3-amino-1,2,4-triazole was dissolved in 100 g of distilled water and 0.101 g (36 wt %, 0.001 mol) of HCl was added thereto, followed by vigorously stirring the resulting solution in an ice water bath at a temperature of 0° C. to 5° C. 1.3 g (5 wt %, 0.001 mol) of $NaNO_2$ was slowly added dropwise to the resulting solution, which in turn was stirred for 1 hour, thereby preparing a salt. 0.133 g (0.001 mmol) of 5-methylbenzotriazole was dissolved in a mixture of 50 g of ethanol and 50 g of ultrapure water, and 4 g of a 2.5 M aqueous NaOH solution was added to the resulting solution, which in turn was added dropwise to the reactor accommodating the salt over 30 minutes. Then, the resulting solution was stirred for 1 hour, followed by decompression and drying, thereby preparing 0.217 g of a compound represented by Formula 1-1. It was confirmed based on the following NMR results that the compound of Formula 1-1 was prepared. NMR results: 1H NMR, 2.4 ppm 3H, 7.0 ppm 1H, 7.6 ppm 1H, 7.7 ppm 1H, 8.0 ppm 1H A CMP slurry composition was prepared by mixing 0.33 wt % of an abrasive agent (colloidal silica, NP60, average particle size: 50 nm), 1.3 wt % of glycine (solid phase, IL Chem) as a complexing agent, 0.02 wt % of the prepared compound of Formula 1-1 as an corrosion inhibitor, 0.3 wt % of 3,5-diamino-1,2,4-triazole, and the balance of ultrapure water, based on the total amount of the CMP slurry composition. The CMP slurry composition was adjusted to pH 7.3 using a pH regulator (nitric acid or potassium hydroxide). After pH regulation, 1.00 wt % of hydrogen peroxide (liquid phase, Dongwoo Fine Chemistry) was added as an oxidizing agent to the CMP slurry composition to prepare a composition for CMP slurry evaluation. In the following table 1, "-" means that a corresponding component was not present.

EXAMPLE 2

0.084 g (0.001 mol) of 3-amino-1,2,4-triazole was dissolved in 100 g of distilled water and 0.101 g (36 wt %, 0.001 mol) of HCl was added thereto, followed by vigorously stirring the resulting solution in an ice water bath at a temperature of 0° C. to 5° C. 1.3 g (5 wt %, 0.001 mol) of $NaNO_2$ was slowly added dropwise to the resulting solution, which in turn was stirred for 1 hour, thereby preparing a salt. 0.119 g (0.001 mmol) of benzotriazole was dissolved in a mixture of 50 g of ethanol and 50 g of ultrapure water, and 4 g of a 2.5 M aqueous NaOH solution was added to the resulting solution, which in turn was added dropwise to the reactor accommodating the salt over 30 minutes. Then, the resulting solution was stirred for 1 hour, followed by decompression and drying, thereby preparing 0.203 g of a compound represented by Formula 1-2.

It was confirmed based on the following NMR results that the compound of Formula 1-2 was prepared. NMR results: 1H NMR, 6.6 ppm 2H, 7.4 ppm 2H, 7.6 ppm 1H A CMP slurry composition was prepared in the same manner as in Example 1 except that the kind and content of each component were changed as listed in Table 1 (unit: wt %).

EXAMPLE 3

0.084 g (0.001 mol) of 3-amino-1,2,4-triazole was dissolved in 100 g of distilled water and 0.101 g (36 wt %, 0.001 mol) of HCl was added thereto, followed by vigorously stirring the resulting solution in an ice water bath at a temperature of 0° C. to 5° C. 1.3 g (5 wt %, 0.001 mol) of $NaNO_2$ was slowly added dropwise to the resulting solution, which in turn was stirred for 1 hour, thereby preparing a salt. 0.084 g (0.001 mmol) of 3-amino-1,2,4-triazole was dissolved in 100 g of ultrapure water, and 4 g of a 2.5 M aqueous NaOH solution was added to the resulting solution, which in turn was added dropwise to the reactor accommodating the salt over 30 minutes. Then, the resulting solution was stirred for 1 hour, followed by decompression and drying, thereby preparing 0.170 g of a compound represented by Formula 1-3. It was confirmed based on the following NMR results that the compound of Formula 1-3 was prepared. NMR results: 1H NMR, 8.1 ppm 2H.

A CMP slurry composition was prepared in the same manner as in Example 1 except that the kind and content of each component were changed as listed in Table 1.

EXAMPLE 4

0.084 g (0.001 mol) of 3-amino-1,2,4-triazole was dissolved in 100 g of distilled water and 0.101 g (36 wt %, 0.001 mol) of HCl was added thereto, followed by vigorously stirring the resulting solution in an ice water bath at a temperature of 0° C. to 5° C. 1.3 g (5 wt %, 0.001 mol) of $NaNO_2$ was slowly added dropwise to the resulting solution, which in turn was stirred for 1 hour, thereby preparing a salt. 0.084 g (0.001 mmol) of 4-amino-1,2,4-triazole was dissolved in 100 g of ultrapure water, and 4 g of a 2.5 M aqueous NaOH solution was added to the resulting solution, which in turn was added dropwise to the reactor accommodating the salt over 30 minutes. Then, the resulting solution was stirred for 1 hour, followed by decompression and drying, thereby preparing 0.170 g of a compound represented by Formula 1-4. It was confirmed based on the following NMR results that the compound of Formula 1-4 was prepared. NMR result: 1H NMR, 7.4 ppm 1H, 7.7 ppm 1H, 8.2 ppm 1H A CMP slurry composition was prepared in the same manner as in Example 1 except that the kind and content of each component were changed as listed in Table 1.

COMPARATIVE EXAMPLES 1 to 3

CMP slurry compositions were prepared in the same manner as in Example 1 except that the kind and content of each component were changed as listed in Table 1.

Polishing evaluation was carried out on the CMP slurry compositions prepared in the Examples and Comparative Examples under the following polishing conditions. Results are shown in Table 1.

(1) Copper polishing rate (unit: Å/min)

A blanket wafer having a diameter of 300 mm and including a copper layer on a silicon oxide layer thereof was polished under the following conditions, followed by calculation of the polishing rate through conversion of a surface resistance variation before and after polishing into an etched thickness.

Polishing machine: Reflexion LK 300 mm (AMAT Co., Ltd.)

Polishing pad: IC1000

Polishing time: Polishing time changed depending upon blanket polishing amount

Head rpm: 87 rpm

Platen rpm: 98 rpm

Flow rate: 200 mL/min

Pressure: 1.0 psi

Measurement of polishing amount: Surface resistance tester (2) Erosion (unit: nm): A polishing solution was left at 60° C. for 1 hour. After polishing a wafer in the same manner as in (1), a pattern profile was measured using an InSight CAP Compact Atomic Profiler (Bruker Co., Ltd.). Erosion was calculated based on a height difference between a peri-oxide and a cell oxide in a 0.18/0.18 μm pattern area of the wafer. A scanning rate was set to 100 μm/sec and a scan length was set to 2 mm.

TABLE 1

| | | Example | | | | Comparative Example | | |
|---|---|---|---|---|---|---|---|---|
| | | 1 | 2 | 3 | 4 | 1 | 2 | 3 |
| Abrasive agent | | 0.33 | 0.33 | 0.33 | 0.33 | 0.33 | 0.33 | 0.33 |
| Corrosion Inhibitor 1 | Formula 1-1 | 0.02 | — | — | — | — | — | — |
| | Formula 1-2 | — | 0.02 | — | — | — | — | — |
| | Formula 1-3 | — | — | 0.02 | — | — | — | — |
| | Formula 1-4 | — | — | — | 0.03 | — | — | — |
| Corrosion Inhibitor 2 | 3,5-diamino-1,2,4-triazole | 0.3 | — | — | — | — | 0.3 | 0.3 |
| | 5-methylbenzotriazole | — | — | — | — | — | 0.01 | — |
| | 1,2,4-triazole | — | — | — | — | 0.2 | — | — |
| Complexing agent | | 1.3 | 1.3 | 1.3 | 1.3 | 1.3 | 1.3 | 1.3 |
| Oxidizing agent | | 1.00 | 1.00 | 1.00 | 1.00 | 1.00 | 1.00 | 1.00 |
| Ultrapure water | | Balance | Balance | Balance | Balance | Balance | Balance | Balance |
| Total amount | | 100 | 100 | 100 | 100 | 100 | 100 | 100 |
| Copper polishing rate | | 9826 | 7421 | 11130 | 7759 | 7604 | 2997 | 9724 |
| Erosion | | 246 | 568 | 624 | 593 | 1767 | 838 | 4241 |

As shown in Table 1, the compound represented by Formula 1 provided a CMP slurry composition that exhibited improved polishing flatness and polishing rate through reduction in erosion upon polishing.

Conversely, the compositions of Comparative Examples, e.g., free from the compound represented by Formula 1, had low polishing flatness and low copper polishing rate.

One or more embodiments may provide a compound that may help improve polishing flatness through reduction in erosion, and polishing rate upon polishing.

One or more embodiments may provide a compound that may be used as a corrosion inhibitor.

One or more embodiments may provide a compound that may help improve polishing flatness through reduction in erosion, and polishing rate upon polishing.

One or more embodiments may provide a CMP slurry composition that may help improve polishing flatness through reduction in erosion, and polishing rate upon polishing.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A CMP slurry composition, comprising:

a polar solvent or a non-polar solvent;

an abrasive agent; and a corrosion inhibitor, wherein the corrosion inhibitor includes a compound represented by Formula 1, or a salt thereof,

[Formula 1]

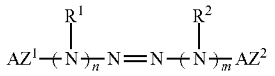

wherein, in Formula 1, $AZ^1$ and $AZ^2$ are each independently a substituted or unsubstituted azole-containing heterocyclic group;

$R^1$ and $R^2$ are each independently hydrogen, a substituted or unsubstituted $C_1$ to $C_{10}$ alkyl group, a substituted or unsubstituted $C_6$ to $C_{20}$ aryl group, a substituted or unsubstituted $C_7$ to $C_{20}$ arylalkyl group, or a substituted or unsubstituted $C_3$ to $C_{20}$ heteroaryl group; and n and m are each independently an integer of 0 to 2.

2. The CMP slurry composition as claimed in claim 1, wherein the azole-containing heterocyclic group of Formula 1 is a monocyclic azole-containing heterocyclic group having 1 to 6 nitrogen atoms or a polycyclic azole-containing heterocyclic group having 1 to 6 nitrogen atoms.

3. The CMP slurry composition as claimed in claim 1, wherein the azole-containing heterocyclic group of Formula 1 is a diazole group, a triazole group, a tetrazole group, a pentazole group, a benzodiazole group, a benzotriazole group, or a naphthotriazole group.

4. The CMP slurry composition as claimed in claim 1, wherein the compound represented by Formula 1 is represented by one of Formulae 1-1 to 1-4:

[Formula 1-1]

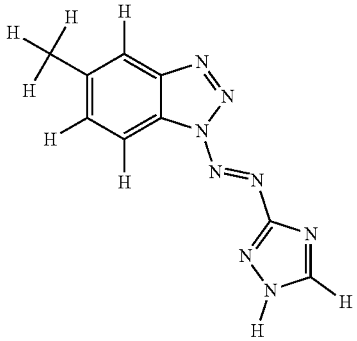

[Formula 1-2]

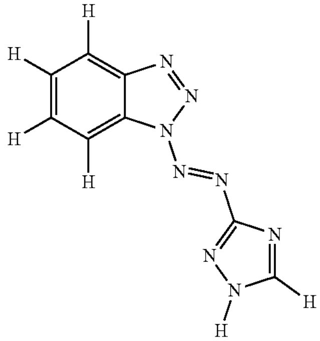

[Formula 1-3]

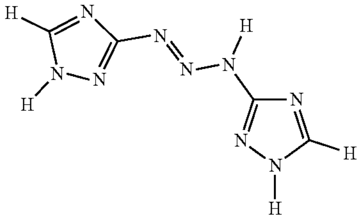

-continued

[Formula 1-4]

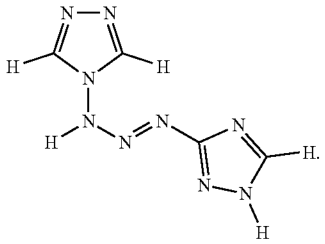

5. The CMP slurry composition as claimed in claim 1, wherein the CMP slurry composition includes 0.001 wt % to 5 wt % of the corrosion inhibitor.

6. The CMP slurry composition as claimed in claim 1, wherein the corrosion inhibitor further includes a diazo group-free corrosion inhibitor.

7. The CMP slurry composition as claimed in claim 6, wherein the diazo group-free corrosion inhibitor includes a triazole corrosion inhibitor or a tetrazole corrosion inhibitor.

8. The CMP slurry composition as claimed in claim 1, further comprising a complexing agent or an oxidizing agent.

9. The CMP slurry composition as claimed in claim 8, wherein the CMP slurry composition includes:

0.001 wt % to 20 wt % of the abrasive agent;

0.001 wt % to 5 wt % of the corrosion inhibitor;

0.01 wt % to 20 wt % of the complexing agent; and 0.1 wt % to 5 wt % of the oxidizing agent.

10. A polishing method comprising polishing a polishing target using the CMP slurry composition as claimed in claim 1.

11. The polishing method as claimed in claim 10, wherein the polishing target is a copper layer.

* * * * *